United States Patent
Thern et al.

(10) Patent No.: US 6,331,775 B1
(45) Date of Patent: Dec. 18, 2001

(54) GAS ZONE EVALUATION BY COMBINING DUAL WAIT TIME NMR DATA WITH DENSITY DATA

(75) Inventors: Holger F. Thern, Houston; Songhua Chen, Katy, both of TX (US)

(73) Assignee: Baker Hughes Incorporated, Houston, TX (US)

( * ) Notice: Subject to any disclaimer, the term of this patent is extended or adjusted under 35 U.S.C. 154(b) by 0 days.

(21) Appl. No.: 09/396,286

(22) Filed: Sep. 15, 1999

(51) Int. Cl.$^7$ .................................................. G01V 3/00
(52) U.S. Cl. ................................................ 324/303
(58) Field of Search ................................ 324/303, 314

(56) References Cited

U.S. PATENT DOCUMENTS

| | | | |
|---|---|---|---|
| 5,023,551 | 6/1991 | Kleinberg et al. | 324/303 |
| 5,517,115 | 5/1996 | Prammer | 324/303 |
| 5,585,720 | 12/1996 | Edwards | 324/309 |
| 5,680,043 | * 10/1997 | Hurlimann et al | 324/303 |
| 5,796,252 | * 8/1998 | Kleinberg et al. | 324/303 |
| 6,005,389 | * 12/1999 | Prammer | 324/303 |
| 6,032,101 | * 2/2000 | Freedman et al. | 702/8 |
| 6,051,973 | * 4/2000 | Prammer | 324/303 |
| 6,140,817 | * 10/2000 | Flaum et al. | 324/303 |
| 6,163,153 | * 12/2000 | Reiderman et al. | 324/314 |

FOREIGN PATENT DOCUMENTS

| | | |
|---|---|---|
| 0871045A2 | 10/1998 | (EP) . |
| WO98/29639 | 7/1998 | (WO) . |

OTHER PUBLICATIONS

Response of Neutron and Formation Density Logs In Hydrocarbon Bearing Formations; R. Gaymard and A. Poupon; The Log Analyst, pp. 3–12.

Lithology–Independent Gas Detection by Gradient–NMR Logging; SPE 30562; M.G. Prammer, et al. NUMAR Corporation; pp 1–12.

NMR Logging of Natural Gas Reservoirs, R. Akkurt, et al.; SPWLA 36th Annual Logging Symposium, Jun. 26–29, 1995; pp. 1–12.

* cited by examiner

Primary Examiner—Hezron Williams
Assistant Examiner—Tiffany A. Fetzner
(74) Attorney, Agent, or Firm—Madan, Mossman & Sriram, P.C.

(57) ABSTRACT

A method for acquiring nuclear magnetic resonance measurements of a medium uses a modified CPMG pulse sequence wherein the refocusing pulses may be optiimized, having a shorter duration than a 180° pulse. Data are acquired in gas reservoirs using two different wait times, both of which are sufficient to polarize the liquid in the reservoir to a known exteny, preferably 100%, while the amount of polarization of the gas in the reservoir is substantially different for the two wait times. Data from the dual wait time NMR pulse sequences give two different apparent porosities of the formation. A third apparent porosity is obtained from density measurements. Combining these three apparent porosities with a temperature measurement and empirical relations between various petrophysical parameters gives the true porosity, the gas density, the gas hydrogen index and the spin-lattice relaxation time of the gas at a single depth. In an alternate embodiment of the invention, apparent porosity measurements made at a plurality of depths within a connected gas reservoir are averaged and, in combination with temperature measurements in the reservoir, the same petrophysical parameters are obtained with the gas properties being constant, thus reducing numerical instability in the solution of the equations relating the petrophysical parameters.

22 Claims, 2 Drawing Sheets

GAS ZONE EVALUATION BY COMBINING DUAL WAIT TIME NMR DATA WITH DENSITY DATA

FIELD OF THE INVENTION

The invention is in the field of determination of petrophysical properties of a partially gas filled medium using data from a Nuclear Magnetic Resonance (NMR) tool and a density tool. More specifically, the method is used to determine porosity, gas saturation and in situ gas density in a hydrocarbon reservoir.

BACKGROUND OF THE INVENTION

A variety of techniques have been utilized in determining the presence and in estimating quantities of hydrocarbons (oil and gas) in earth formations. These methods are designed to determine formation parameters, including among other things, porosity, fluid content and permeability of the rock formation surrounding the wellbore drilled for recovering hydrocarbon. Typically, the tools designed to provide the desired information are used to log the wellbore. Much of the logging is done after the well bores have been drilled. More recently, wellbores have been logged while drilling of the wellbores, which is referred to as measurement-while-drilling ("MWD") or logging-while-drilling ("LWD"). Measurements have also been made when tripping a drillstring out of a wellbore: this is called measurement-while-tripping ("MWT").

One recently evolving technique involves utilizing Nuclear Magnetic Resonance (NMR) logging tools and methods for determining, among other things porosity, hydrocarbon saturation and permeability of the rock formations. The NMR logging tools are utilized to excite the nuclei of the of the fluids in the geological formations in the vicinity of the wellbore so that certain parameters such as spin density, longitudinal relaxation time (generally referred to in the art as "$T_1$") and transverse relaxation time (generally referred to as "$T_2$") of the geological formations can be estimated. From such measurements, porosity, permeability and hydrocarbon saturation are determined, which provides valuable information about the make-up of the geological formations and the amount of extractable hydrocarbons.

A typical NMR tool generates a static magnetic field $B_0$ in the vicinity of the wellbore, and an oscillating field $B_1$ in a direction perpendicular to $B^0$. This oscillating field is usually applied in the form of short duration pulses. The purpose of the $B_0$ field is to polarize the magnetic moments of nucleii parallel to the static field and the purpose of the $B_1$ field is to rotate the magnetic moments by an angle $\theta$ controlled by the width $t_p$ and the amplitude $B_1$ of the oscillating pulse. With the variation of the number of pulses, pulse duration and pulse intervals, various pulse sequences can be designed to manipulate the magnetic moment, so that different aspects of the NMR properties can be obtained. For NMR logging, the most common sequence is the Carr-Purcell-Meiboom-Gill ("CPMG") sequence that can be expressed as $$TW-90-(t-180-t-echo)_n$$

After being tipped by 90°, the magnetic moment precesses around the static field at a particular frequency known as the Larmor frequency $\omega_0$, given by $\omega_0=\gamma B_0$, where $B_0$ is the field strength of the static magnetic field and $\gamma$ is the gyromagnetic ratio. At the same time, the single magnetic moments return to the equilibrium direction (i.e., aligned with the static field) according to a decay time known as the "spin-lattice relaxation time" or $T_1$. Inhomogeneities of the $B_0$ field result in dephasing of the magnetic moments and to remedy this, a 180° pulse is included in the sequence to refocus the magnetic moments. This gives a sequence of n echo signals.

U.S. Pat. No. 5,023,551 issued to Kleinberg discloses an NMR pulse sequence that has an NMR pulse sequence for use in the borehole environment which combines a modified fast inversion recovery (FIR) pulse sequence with a series of more than ten, and typically hundreds, of CPMG pulses according to $$[W_i-180-TW_i-90-(t-180-t-echo)_j]_1$$

where j=1,2, . . . J and J is the number of echoes collected in a single Carr-Purcell-Meiboom-Gill (CPMG) sequence, where i=1, . . . I and I is the number of waiting times used in the pulse sequence, where $W_i$ are the recovery times, $TW_i$ are the wait times before a CPMG sequence, and where t is the spacing between the alternating 180° pulses and the echo signals.

Proton NMR measurement is typically performed for logging since hydrogen is abundant in reservoir fluids. T2 is very short in solids, but relatively long in liquids and gases, so that the NMR signal from the solid rock decays quickly and only the signal from fluids in the rock pores in the region of interest is seen. This signal may arise from hydrogen in hydrocarbon or water within the pores of the formation. The local environment of the hydrogen influences the measured T2 or "spin-spin" relaxation. For example, capillary bound fluid has a shorter T2 than fluid in the center of a pore, the so-called "free fluid." In this way, the NMR tool can be used advantageously to distinguish between producible fluid and non-producible fluid.

The NMR echo signals provide information about fluid and rock properties. Depending upon the goal of the investigation, various NMR measurement techniques can be used to obtain different petrophysical properties (e.g., partial and total porosities) or to discern multiphase fluids for hydrocarbon typing purposes. The different NMR acquisition techniques are characterized by differences in pulse timing sequences as well as repetition times between measurements. In addition, in wireline applications, multiple runs of NMR acquisition sequences with different parameters can be combined to enhance the analysis of the desired petrophysical information. However, in measurement-while-drilling applications or in measurement-while-tripping applications, it is not possible to make multiple runs, so that all the desired information must be obtained at one time while the borehole is being drilled or tripped.

Several methods to identify and quantify gas reservoirs have been employed during the last few years utilizing the effect of different wait times on the measured NMR signal. Depending upon the fluid properties, the wait time (TW) determines the amount of the polarized medium that contributes to the measured signal. For example, Akkurt et.al. disclose a Differential Spectrum Method (DSM) based upon this effect in their paper "NMR Logging of Natural Gas Reservoirs" presented at the 36th Annual Meeting of the Society of Professional and Well Log Analysts (SPWLA) in 1995. Another related technique is the Time Domain Analysis (TDA) presented in the 1995 Society of Petroleum Engineers meeting by Prammer et. al. in a paper entitled "Lithology-Independent Gas Detection by Gradient NMR Logging." These techniques require the calculation of differential echo signals or differential $T_2$ spectra that are derived from the echo trains by an inversion. The differential quantities are derived from two echo train data acquired with different wait times by subtracting either the echo train data or their $T_2$ spectra. As would be known to those versed in the art, this subtraction of one noisy signal from a second noisy signal leads to a reduction in signal-to-noise ratio. This, coupled with the low hydrogen density of a gaseous hydrocarbon, is a major problem in accurately estimating reservoir properties.

European Patent Application 0 871 045 of Freedman discloses a method in which an oscillating magnetic field is produced according to the Carr-Purcell-Meiboom-Gill (CPMG) sequence to induce NMR echo signals. The spin echo signals are separated into a first set and a second set wherein the first set comprises the early-time echo signals and the second set comprises the remaining echo signals. The second set of echo signals are subdivided into a plurality of groups and a window sum value is generated for each group of the second set, producing a plurality of window sums.

In formations having a gas saturation, the porosity as determined by a conventional density tool needs to be corrected because the presence of the gas phase causes the porosity to be overestimated. On the other hand, an NMR-derived porosity obtained using a CPMG sequence wherein TW is sufficiently long to substantially polarize all the formation fluid in the sensitive volume underestimates the true porosity. Solving a system of two equations, the true porosity is then obtained as a function of the NMR derived porosity, the density derived porosity, and a hydrogen index of the liquid phase $HI_l$ in the flushed zone at reservoir conditions.

$$\Phi = wPORZ + (1-w)TPOR/HI_l$$

where PORZ is the porosity derived from the density measurement, TPOR is the NMR-derived porosity. The value of w depends, among other factors, on the hydrogen index of the gas phase $HI_g$, the CPMG pulse sequence TW and the longitudinal NMR relaxation time of the gas $T_{1,g}$. Freedman suggests that a quick estimate of the porosity can be obtained by using a value of 0.6 for w, and using a value for $HI_l$ of 1.0, so that the true porosity becomes a weighted average of the density derived porosity and NMR derived porosity.

There is a need for a method of obtaining the porosity and gas saturation of a reservoir more accurately and without making the approximation of using a constant weighting factor w. There is also a need to characterize the gas phase by the spin-lattice relaxation time of the gas $T_{1g}$, the hydrogen index of the gas $HI_g$, and density of the gas $\rho_g$ in order to derive the gas saturation $S_{g,xo}$ of the reservoir. The present invention satisfies this need.

SUMMARY OF THE INVENTION

The invention is a method for acquiring nuclear magnetic resonance measurements of a porous medium and determining the total porosity and gas saturation of a partially gas filled medium. The method includes inducing an external static magnetic field in the material, and applying a radio frequency pulse to tip the spins by 90°. The resulting precession of the spins is detected by a receiver coil. A refocusing pulse having a spin tip angle substantially less than 180° is applied. Measurements are made with two different "wait times" in the NMR pulse sequence to give two different apparent porosities of the medium. When combined with a density measurement using a conventional density logging tool, the gas saturation and porosity of a medium can be determined with higher accuracy than in prior art methods without making the assumptions used therein. The method also includes estimation of certain properties of the gas.

DESCRIPTION OF THE PREFERRED EMBODIMENT

Figure 1:
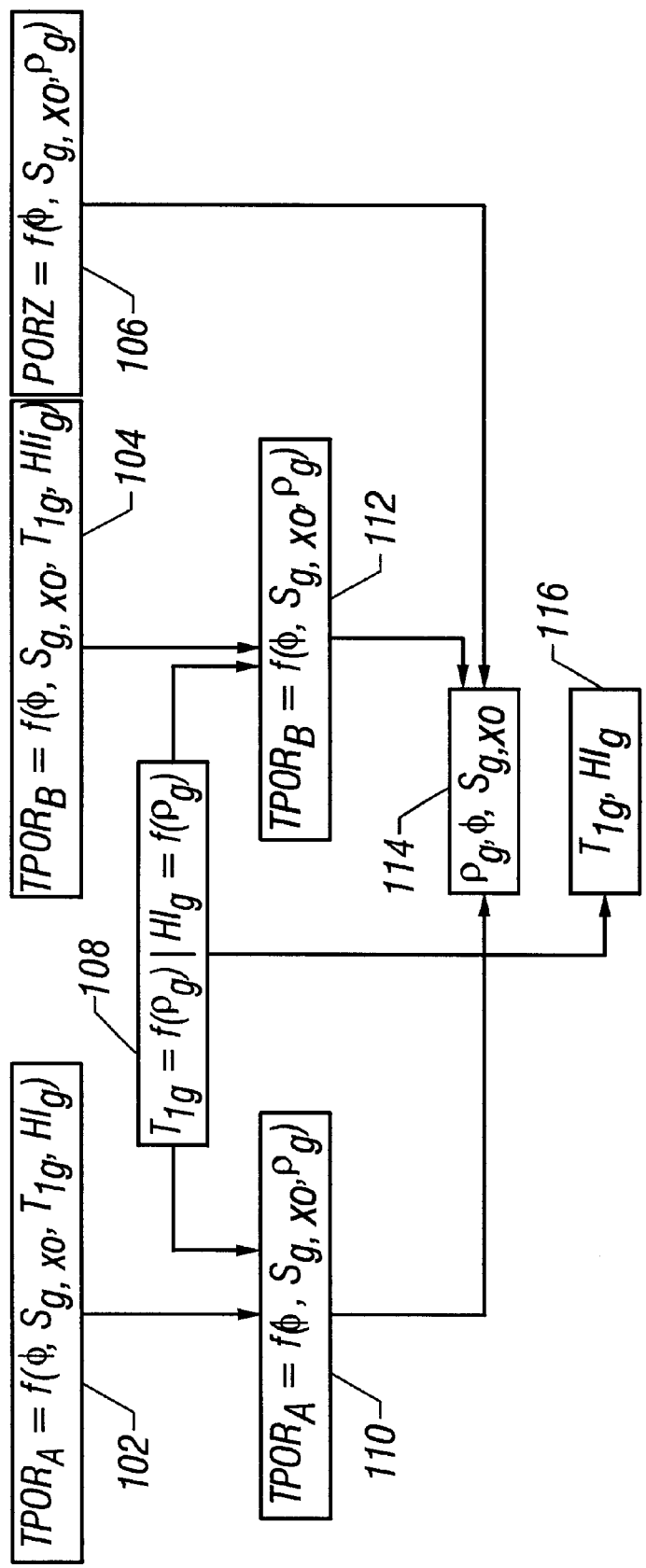
FIG. 1 illustrates an embodiment of the invention in which determination of the parameters of interest of a formation is done at a single depth of a gas reservoir.

A typical nuclear magnetic resonance ("NMR") instrument which can make measurements according to this invention is described, for example, in U.S. Pat. No. 5,585,720 issued to Edwards, the contents of which are fully incorporated herein by reference. The instrument described in the Edwards '720 patent includes a permanent magnet for inducing a static magnetic field within the medium to be analyzed. In particular, the medium to be analyzed can include earth formations surrounding a wellbore. The instrument in the Edwards '720 patent includes an antenna coil which can be wound around the magnet, circuitry for applying pulses of radio-frequency (RF) power to the antenna coil, and circuitry for detecting voltages induced in the antenna coil as a result of nuclear magnetic resonance phenomena, particularly that of hydrogen nuclei present in the earth formations.

As is known in the art, the RF pulses applied to the antenna coil of NMR apparatus such as the one in the Edwards '720 patent typically include an initial RF pulse having a duration and amplitude which reorients the nuclear spin axes of the hydrogen nuclei in the earth formations so that they become substantially perpendicular to the direction of the static magnetic field induced by the magnet. This first RF pulse induces an angular deflection of about 90 degrees in the spin axes of the hydrogen nuclei. Later in the measurement cycle known in the art, a sequence of additional RF pulses (referred to as "refocusing pulses"), each having a duration and amplitude selected to reorient the extant nuclear spin axes by 180 degrees, is applied to the antenna coil. In between refocusing pulses, the antenna coil is connected to a receiver circuit to detect voltages induced in the antenna coil as the nuclear spin axes "rephase", an event called the pulse-echo or spin echo. The combination of tipping pulses and refocusing pulses is known as a Carr-Purcell-Meiboom-Gill (CPMG) sequence. As is understood by those skilled in the art, the amplitude of the induced voltages from spin rephasing (pulse-echo voltages) decreases after each successive refocusing pulse applied to the antenna coil. The rate at which the amplitude of the successive pulse-echo voltages decays is related to properties of the earth formations such as fractional volume of pore space and the bulk volume of mobile fluids filling the pore space, as is known in the art.

In co-pending U.S. application Ser. No. 09/151,871, having the same assignee as the present application and the contents of which are incorporated herein by reference, it has been disclosed that the refocusing pulses should preferably have a duration and amplitude selected to cause the nuclear spin axes to reorient by an angular deflection different from 180 degrees, and between 100° and 135°. With such a refocusing pulse, the power requirements are reduced and the signal to noise ratio of the echos is improved.

Accordingly, the RF field of the present invention includes a pulse sequence $$TW-90_{\pm x}-(t-X-t-echo)_j \qquad (1)$$

where TW is a wait time, $90_{\pm x}$ represent tipping pulses for tipping the nuclear spins at an angle substantially equal to ninety degrees to cause precession thereof, t is the spacing between the alternating refocusing pulse and the echo signal, X is an optimized refocusing pulse, and j=1,2, . . . J, where J is the number of echoes collected in a single sequence of pulses.

The present invention is a method for evaluating the petrophysical properties of a gas reservoir including one gas phase and one liquid phase. The method combines the apparent porosities $TPOR_A$ and $TPOR_B$ of a dual wait time NMR measurement obtained using wait times of $TW_A$ and $TW_B$ respectively with the apparent porosity PORZ of a density measurement and obtains the true porosity $\Phi$ of the gas zone, the gas saturation $S_{g,xo}$ in the gas zone, the gas density $\rho_g$ in the gas zone, the hydrogen index $HI_g$ of the gas zone, and, the spin-lattice relaxation time of the gas $T_{1g}$. A depth-dependent formation temperature is obtained during the acquisition of the NMR or density data, while the matrix density $\rho_{ma}$ is obtained from external information, such as sample measurements or interpretations of other logs.

In a two-phase system with one gas and one liquid phase, the apparent total porosity TPOR as measured by an NMR tool is given by $$TPOR = \Phi S_{g,xo} HI_g P_g + \Phi(1-S_{g,xo}) HI_l P_l \qquad (2)$$

where the first term describes the contribution of the gas phase and the second term the contribution of the liquid phase. $\Phi$ here denotes the porosity of the formation, $HI_g$ and $HI_l$ are the hydrogen indices of the gas phase and the liquid phase respectively, $S_{g,xo}$ is the gas saturation, and $P_g$ and $P_l$ are the polarizations of the gas and liquid phases respectively produced by the NMR signal. These are related to the wait time TW of the NMR signal by $$P_g = 1 - e^{-\frac{TW}{T_{1g}}} \qquad (3)$$

and $$P_l = 1 - e^{-\frac{TW}{T_{1l}}} \qquad (4)$$

As would be known to those versed in the art, equation (2) is valid only if the apparent porosity is determined using a long CPMG sequence to obtain the $T_2$ distribution. A number of simplifications may be made for most liquids without detracting from the scope of the invention. For an aqueous phase liquid and for most hydrocarbons, the value of $HI_l$ is close to 1. The polarization effects of liquids $P_l$ is negligible if the spin lattice relaxation time $T_{1l}$ is much smaller than the wait time TW. Typically, TW ranges from 1 to several seconds, whereas a typical aqueous phase liquid has a $T_{1l}$ in the range of 1 to several hundred milliseconds in a two-phase system. Thus, $P_l$ can usually be taken to be equal to 1 in a two-phase system.

The present invention determines the apparent porosity from NMR measurements using a pulse sequence having two different wait times $TW_A$ and $TW_B$. This is done by using an RF field including a first pulse sequence $TW_A$–90–$(t_{cp}-X-t_{cp}-echo)_j$ and a second pulse sequence $TW_B$–90–$(t_{cp}-X-t_{cp}-echo)_j$, wherein $TW_A$ is a first waiting time and $TW_B$ is a second wait time different from the first wait time. In a preferred embodiment of the invention, the dual wait time echo signals are obtained in a single pass of the logging instrument. In an alternate embodiment of the invention when measurements are made using a wireline device, the echo signals for the first and second wait times may be obtained in two different passes of the logging instrument.

Under these assumptions, the apparent porosities for the dual wait time NMR device may be written as $$TPOR_A = \Phi S_{g,xo} HI_g \left[ 1 - e^{-\frac{TW_A}{T_{1g}}} \right] + \Phi(1-S_{g,xo}) HI_l P_l \qquad (5)$$

and $$TPOR_B = \Phi S_{g,xo} HI_g \left[ 1 - e^{-\frac{TW_B}{T_{1g}}} \right] + \Phi(1-S_{g,xo}) HI_l P_l \qquad (6)$$

In one embodiment of the invention, the hydrogen index of the liquid phase $HI_l$ and the polarization of the liquid phase $P_l$ are taken to be one. However, if the formation includes oleic phase liquids or a mixture of oleic and aqueous liquids, those versed in the art would recognize the that these two quantities cannot be taken as equal to one. An alternate embodiment of the invention uses externally derived values for $HI_l$ and $P_l$.

The wait times $TW_A$ and $TW_B$ are chosen so that they substantially polarize the liquid, i.e., $P_l(TW_A) \approx P_l(TW_B) \approx 1$, while the polarization of the gas in the formation is substantially different for $TW_A$ and $TW_B$.

The density $\rho_b$ measured by a density tool is given by $$\rho_b = \rho_{ma}(1-\Phi) + \rho_f \Phi(1-S_{g,xo}) + \rho_g \Phi S_{g,xo} \qquad (7)$$

Using the relation $$PORZ = \frac{\rho_{ma} - \rho_b}{\rho_{ma} - \rho_l} \qquad (8)$$

the apparent total porosity measured by a density tool for a two phase fluid system can be written as $$PORZ = \Phi + \Phi S_{g,xo} \frac{\rho_f - \rho_g}{\rho_{ma} - \rho_l} \qquad (9)$$

In the present invention, the matrix density $\rho_{ma}$ is obtained from other measurements, such as interpreted logs or core plugs and is, in general, constant over the particular reservoir being investigated. For example, $\rho_{ma}$ is 2.65 g/cc for sandstones while values for other common reservoir rocks such as limestones and dolomites would be known to those versed in the art. In one embodiment of the invention, the liquid density $\rho_l$ is approximately 1.0 g/cc for aqueous liquids while in an alternate embodiment of the invention, for an oleic reservoir liquid, the density a lower density, e.g., 0.8–0.9 g/cc, is used.

In the present invention, the temperature of the reservoir is determined by a suitable temperature sensor. Based on measurement and theory, the spin-lattice relaxation time of the gas $T_{1g}$ is related to the temperature and density of the gas by an equation of the form $$T_{1g} = \frac{B}{T_K^C} \rho_g \qquad (10)$$

where B is a constant for a single gas phase with constant volumetrics and C has a theoretical value of 1.5. In equation (1), $T_K$ is the temperature of the gas in degrees Kelvin, i.e., the absolute temperature. Experimental data, such as that published by Gerritsma and Trappeniers may be used to determine empirical values for B and C.

Based on the definition of the Hydrogen Index, there is a linear relationship between the gas hydrogen index and the gas density $$HI_g = A \rho_g \qquad (11)$$

For every known hydrocarbon or known mixture of hydrocarbons, the factor A can be calculated exactly. Gaymard and Poupon in their paper "Response of Neutron and Formation Density Logs in Hydrocarbon Bearing Formations" found an approximate value of A=2.2 for hydrocarbons with density less than 0.25 g/cc in the gaseous phase. For pure methane, the exact value of A is 2.25.

Equations 5, 6, 9, 10 and 11 are five equations in five unknowns $\Phi$, $S_{g,xo}$, $\rho_g$, $HI_g$ and $T_{1g}$. They may be solved using the assumptions discussed above for the five unknowns.

Equations 5 and 6 show that $TPOR_A$ and $TPOR_B$ are functions of four variables $$TPOR_A = f_1(\Phi, S_{g,xo}, HI_g, T_{1g}) \qquad (12)$$

$$TPOR_B = f_2(\Phi, S_{g,xo}, HI_g, T_{1g}) \qquad (13)$$

Substituting from equations (10) and (11) reduces (12) and (13) to equations of the form $$TPOR_A = f_3(\phi, S_{g,xo}, \rho_g) \qquad (14)$$

and $$TPOR_B = f_4(\Phi, S_{g,xo}, \rho_g) \qquad (15)$$

Equation (9) is already in the form $$PORZ = f_5(\Phi, S_{g,xo}, \rho_g) \qquad (16)$$

The system of five equations in five unknowns is now reduced to three equations in three unknowns. These may be solved numerically using known methods to obtain $\Phi$, $S_{g,xo}$ and $\rho_g$. By back substituting the value of $\rho_g$ in equations (10) and (11), $HI_g$ and $T_{1g}$ may be determined.

A preferred embodiment of the present invention involves the following steps:

1. Obtain NMR measurements using at least two different wait times $TW_A$ and $TW_B$.
2. Analyze the results of step (1) using known techniques to obtain apparent total porosities $TPOR_A$ and $TPOR_B$.
3. Determine an apparent total porosity PORZ from density measurements.
4. Substitute from equations (10) and (11) in equations (5) and (6) to give equations of the form (14) and (15).
5. Using the density measurement and the derived apparent total porosity, solve equations (14)–(16) to determine the true porosity, the gas saturation and the gas density. This may be done numerically using known methods.
6. Substitute the determined gas density from step 5 into equation (10) and (11) to get the spin-lattice relaxation time of the gas $T_{1g}$ and the hydrogen index of the gas.

Steps 1–6 are schematically represented in FIG. 1. 102, 104 and 106 are the representations of equations (12), (13) and (16) Substituting firm equations (9) and (11) (Box 108), equations (14) and (15) are obtained (boxes 110, 112). Solution of equations (16), (14) and (15) gives the gas density $\rho_g$, the true porosity $\Phi$ and the gas saturation $S_{g,xo}$, (box 114). Using the information in 114 in equations (9) and (11) (box 108) gives the hydrogen index of the gas and the spin-lattice relaxation time of the gas $T_{1g}$ (116).

Those versed in the art would recognize that solution of five equations for five unknowns using noisy measurements may occasionally lead to numerical instabilities. Accordingly, in such cases, an alternate embodiment of the invention using multiple measurements within a single gas reservoir may be used.

Figure 2:
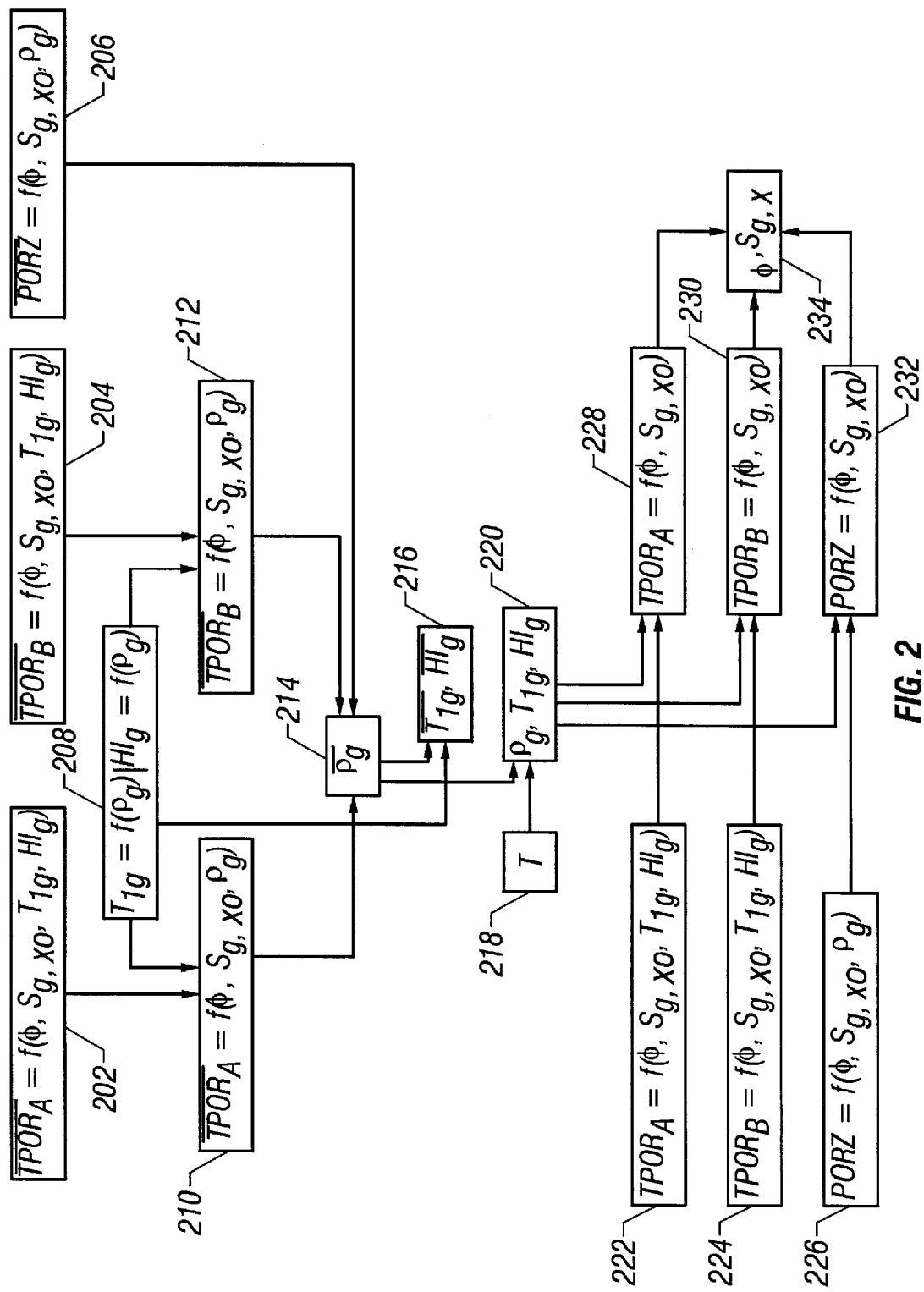
FIG. 2 illustrates an embodiment of the invention in which determination of the parameters of interest of a formation is done using data from a plurality of depths within a single, connected gas reservoir.

This method assumes that measurements are made at a plurality of depths within a single connected gas reservoir with substantially uniform gas composition. Turning now to FIG. 2, the observations at the plurality of depths are processed separately to give three different apparent porosities. These values are then averaged over the plurality of depths to give three averaged apparent porosities 202, 204 and 206. Equations (9) and (11) (box 208) are used to express the average apparent NMR porosities as functions of porosity, gas saturation and gas density (210 and 212). These functional relations are combined with the averaged density-derived apparent porosity to give an average gas density at 214 and average values of the hydrogen index $H_{Ig}$ and spin-lattice relaxation time of the gas $T_{1g}$, (Box 216).

A plurality of temperature measurements are made in the reservoir to give a temperature profile 218. As would be known to those versed in the art, pressure, volume and temperature of a gas are related by an equation of state. One such equation of state is that developed by van der Waal:

$$\left(p + \frac{n^2 a}{V^2}\right)(V - nb) = nRT \qquad (17)$$

where p is the pressure, V is the volume, n is the number of moles of gas, R is the gas constant, T is the absolute temperature, and a and b are constants depending upon the type of gas. The values for p, V, n and R are well-defined and values for a and b may be found in tables. Using this, or any other suitable equation of state for a gas, the measured temperature of the reservoir as a function of depth, and a depth dependent pressure gradient, the gas density as a function of depth is determined from the average gas density. The depth dependent pressure gradient, as would be known to those versed in the art, is approximately 0.433 psi/ft for normally pressured formations. From this density profile, a depth profile of the hydrogen index and the gas relaxation time may be obtained (box 220).

At this point, the processing may be performed at individual depths using the information in 220 with the three apparent porosities 222, 224, 226. These may be expressed as functions of two variables (Box 228, 230, 232) (the true porosity and the gas saturation) as an overdetermined set of equations and solved by known methods to give the porosity and gas saturation (Box 234) at each depth. One advantage of using the method of FIG. 2 is that averaged values of the apparent porosities are used in the determination of the average gas density, the average hydrogen index of the gas, and the average spin-lattice relaxation time of the gas, thereby avoiding possible numerical instability that could arise in the method of FIG. 1 and increasing the accuracy of the estimated properties.

Those skilled in the art will devise other embodiments of this invention which do not depart from the spirit of the invention as disclosed herein. Accordingly, the invention should be limited in scope only by the attached claims.

What is claimed is:

1. A nuclear magnetic resonance method for using a borehole tool in a borehole for determining a plurality of parameters of interest of a volume of earth formation in a reservoir adjacent the borehole, the method comprising:

(a) using a magnet assembly on the borehole tool at at least one depth for producing a static magnetic field in said volume of the formation thereby aligning nuclear spins within said volume parallel to a direction of the static field;

(b) producing a radio frequency (RF) magnetic field in said volume of the formation with an antenna on the borehole tool, said RF magnetic field having a direction orthogonal to a direction of the static field, the RF field including a first pulse sequence $TW_A$–90–(t–X–t–echo)$_j$ and a second pulse sequence $TW_B$–90–(t–X–t–echo)$_j$, wherein 90 is a tipping pulse for tipping the nuclear spins at an angle substantially equal to ninety degrees to cause precession thereof, $TW_A$ is a waiting time, $TW_B$ is a second waiting time different from the first waiting time, X is a refocusing pulse, and j=1, 2, . . . J, where J is the number of echoes collected in a single sequence of pulses;

(c) measuring with the borehole tool signals inaduced by the pulsed RF field in the formation;

(d) obtaining a bulk density measurement of the earth formation at the at least one depth; and (e) using a processor for determining a first apparent porosity $TPOR_A$ and a second apparent porosity $TPOR_B$ associated with the first and second pulse sequences respectively from the induced signals at the at least one depth and determining therefrom and from the obtained bulk density the plurality of parameters of interest;

wherein said first and second apparent porosities are different from each other and are determined in part from a polarization of the spins produced by the associated pulse sequence.

2. The method of claim 1 wherein the first pulse sequence and the second pulse sequence are applied in one or more logging passes.

3. The method of claim 1 wherein the reservoir comprises at least one gas zone, the method further comprising obtaining a temperature $T_{[K]}$ of the at least one gas zone at the at least one depth.

4. The method of claim 3 wherein obtaining said bulk density mesurement further comprises using a density measurement tool.

5. The method of claim 4 wherein the plurality of parameters of interest includes (i) a true total porosity $\Phi$ of the gas zone, (ii) a gas saturation ($S_{g,xo}$) in the gas zone, (iii) a gas density $\rho_g$ in the gas zone, (iv) a hydrogen index ($HI_g$) of the gas zone, and, (v) a spin-lattice relaxation time of the gas ($T_{1g}$).

6. The method of claim 5 wherein using the processor includes using a relation between $T_{1g}$, the gas density $\rho_g$ of the gas zone and $T_{[K]}$ of the form:

$$T_{1g}=B\rho_g/T^C_{[K]}.$$

7. The method of claim 6 wherein using the processor includes using a relation between $HI_g$ and $\rho_g$ of the form $HI_g=A\rho_g$.

8. The method of claim 6 wherein using the processor includes using a relation between $TPOR_A$, $\Phi$, $T_{1g}$, $S_{g,xo}$, $HI_g$, and $TW_A$ of the form $$TPOR_A=\Phi S_{g,xo}HI_g[1-\exp(-TW_A/T_{1g})]+\Phi(1-S_{g,xo})HI_lP_l.$$

9. The method of claim 8 wherein $HI_l$ and $P_l$ are taken to have a value of 1.

10. The method of claim 3 wherein the at least one gas zone includes a liquid therein, and wherein $TW_A$ and $TW_B$ are taken to give a known value of the polarization of the liquid in the formation, while the amount of polarization of the gas in the formation is substantially different for $TW_A$ and $TW_B$.

11. The method of claim 10 wherein the known polarization of the liquid in the formation is substantially equal to one.

12. The method of claim 1 wherein the at least one depth further comprises a plurality of depths in a gas zone having gas therein, the method further comprising obtaining a temperature of the gas zone at the plurality of depths.

13. The method of claim 12 wherein the first pulse sequence and the second pulse sequence are applied in one or more logging passes.

14. The method of claim 12 wherein obtaining said bulk density measurement further comprises using a density measurement tool at each of the plurality of depths.

15. The method of claim 14 wherein using the processor further comprises obtaining an average gas density $\rho_g$, an average hydrogen index of the gas $HI_g$, and an average spin-lattice relaxation time of the gas $T_{1g}$.

16. The method of claim 15 further comprising using said temperature at the plurality of depths, said average density of the gas, said average hydrogen index of the gas and said average spin-lattice relaxation time of the gas for obtaining a gas density, a hydrogen index of the gas and a spin lattice relaxation time of the gas at the plurality of depths.

17. The method of claim 16 wherein obtaining the gas density, the hydrogen index of the gas and the spin lattice relaxation time of the gas at the plurality of depths further comprises using an equation of state for the gas.

18. The method of claim 16 further comprises using said obtained gas density, the hydrogen index of the gas, the spin lattice relaxation time of the gas at the plurality of depths, the first apparent porosity, the second apparent porosity and the bulk density at the plurality of depths for determining the porosity of the gas zone and a gas saturation of the gas zone at each of the plurality of depths.

19. The method of claim 18 wherein determining the porosity of the gas zone and a gas saturation of the gas zone at each of the plurality of depths further comprises solving an overdetermined set of equations.

20. The method of claim 1 wherein the refocusing pulse is an optimized refocusing pulse.

21. The method of claim 11 wherein the refocusing pulse is an optimized refocusing pulse.

22. The method of equation 15 wherein the equation of state for the gas is given by van der Waal's equation.

* * * * *